United States Patent
Sugiyama et al.

(10) Patent No.: US 11,285,096 B2
(45) Date of Patent: *Mar. 29, 2022

(54) CORE-CORONA POLYMER PARTICLES

(71) Applicant: Shiseido Company, Ltd., Tokyo (JP)

(72) Inventors: Yuki Sugiyama, Kanagawa (JP); Ryushi Fukuhara, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/982,315

(22) PCT Filed: Mar. 22, 2019

(86) PCT No.: PCT/JP2019/012145
§ 371 (c)(1),
(2) Date: Sep. 18, 2020

(87) PCT Pub. No.: WO2019/182126
PCT Pub. Date: Sep. 26, 2019

(65) Prior Publication Data
US 2021/0007965 A1   Jan. 14, 2021

(30) Foreign Application Priority Data
Mar. 23, 2018   (JP) .............................. JP2018-057271

(51) Int. Cl.
*A61K 8/91* (2006.01)
*C08F 290/06* (2006.01)
(Continued)

(52) U.S. Cl.
CPC .............. *A61K 8/91* (2013.01); *A61K 8/0245* (2013.01); *A61K 8/062* (2013.01); *A61K 8/064* (2013.01);
(Continued)

(58) Field of Classification Search
None
See application file for complete search history.

(56) References Cited

U.S. PATENT DOCUMENTS

| | | |
|---|---|---|
| 6,440,399 B1 | 8/2002 | Gers-Barlag et al. |
| 2008/0175809 A1 | 7/2008 | Sakuta et al. |
| | | (Continued) |

FOREIGN PATENT DOCUMENTS

| | | |
|---|---|---|
| JP | 01-284516 A | 11/1989 |
| JP | 2001-518111 A | 10/2001 |
| | (Continued) | |

OTHER PUBLICATIONS

Kaneda et al., "Swelling behavior of PMMA-g-PEO microgel particles by organic solvents," Journal of Colloid and Interface Science, 2004, 274:49-54.

*Primary Examiner* — Dominic Lazaro
(74) *Attorney, Agent, or Firm* — Foley & Lardner LLP (57) ABSTRACT

Provided are a raw material for a cosmetic and an oil-in-water emulsion cosmetic comprising a core-corona polymer particle excellent in emulsion stability and feeling of use. Certain embodiments of the present invention provides a raw material for a cosmetic, comprising a core-corona polymer particle dispersion obtained by radical-polymerizing a polyethylene oxide macromonomer represented by formula (1) and one or two or more of hydrophobic monomers represented by formulas (2) and (3) under conditions (A) to (D).

8 Claims, 1 Drawing Sheet

(51) Int. Cl.
*A61K 8/06* (2006.01)
*A61K 8/02* (2006.01)
*A61Q 19/00* (2006.01)

(52) U.S. Cl.
CPC .......... *A61Q 19/00* (2013.01); *C08F 290/068* (2013.01); *A61K 2800/10* (2013.01); *A61K 2800/26* (2013.01)

(56) References Cited

U.S. PATENT DOCUMENTS

| | | |
|---|---|---|
| 2012/0172457 A1 | 7/2012 | Braun et al. |
| 2014/0341957 A1 | 11/2014 | Yang et al. |
| 2014/0343170 A1 | 11/2014 | Sugiyama et al. |
| 2016/0001244 A1* | 1/2016 | Sugiyama .............. A61Q 13/00 512/1 |
| 2017/0239165 A1 | 8/2017 | Sugiyama et al. |
| 2019/0015318 A1 | 1/2019 | Moriya |

FOREIGN PATENT DOCUMENTS

| | | |
|---|---|---|
| JP | 2002-322219 A | 11/2002 |
| JP | 2003-055164 A | 2/2003 |
| JP | 2005-015623 A | 1/2005 |
| JP | 2005-213448 A | 8/2005 |
| JP | 2005-213485 A | 8/2005 |
| JP | 2006-161026 A | 6/2006 |
| JP | 2010-285610 A | 12/2010 |
| JP | 2012-241004 A | 12/2012 |
| JP | 2014-534275 A | 12/2014 |
| JP | 2015-091964 A | 5/2015 |
| WO | WO-2006/051746 A1 | 5/2006 |
| WO | WO-2013/094298 A1 | 6/2013 |
| WO | WO-2016/021338 A1 | 2/2016 |
| WO | WO-2017/187750 A1 | 11/2017 |

* cited by examiner

CORE-CORONA POLYMER PARTICLES

RELATED APPLICATION

The present application is the U.S. National Stage of PCT/JP2019/012145, filed Mar. 22, 3019, which claims the priority of Japanese Patent Application No. 2018-057271 filed on Mar. 23, 2018, which is incorporated herein.

FIELD OF THE INVENTION

The present invention relates to a core-corona polymer particle. Particularly, the present invention relates to improvement in the emulsion stability and usability of a cosmetic containing the same.

BACKGROUND OF THE INVENTION

For stably dispersing a liquid in another liquid, emulsion cosmetics in the conventional sense require adding a surface-active substance (emulsifier). The emulsifier has an amphiphilic molecular structure and is constituted by polar (hydrophilic) and nonpolar (hydrophobic) moieties.

In emulsion cosmetics for use in cosmetic products, etc., aqueous components and oil components are stably mixed by the emulsifying effect of an added surfactant. Oil-in-water cosmetics are reportedly excellent in feeling of use that confers watery texture because dispersed microdroplets of the oil phase are surrounded by emulsifier shells and the external phase is a continuous water phase. Also, water-in-oil emulsion cosmetics have good spreadability upon application and an excellent water-resistant effect of a makeup film after application because microdroplets of the water phase are dispersed in a continuous oil phase.

Meanwhile, as an increasing number of consumers have placed more emphasis on safety in recent years, some hypersensitive users have a growing demand for oil-in-water emulsion cosmetics or water-in-oil emulsion cosmetics free from even a surfactant that might give irritancy to the skin on rare occasions or containing the surfactant at a content without giving such irritation.

Surfactants have the property of forming a high-order associate with poor feeling of use in association with the elevation of a relative concentration with respect to water or an oil. Therefore, emulsion cosmetics using a surfactant as an emulsifier may impair refreshing feeling and cause stickiness or sliminess due to the elevation of the surfactant concentration of a makeup film in association with solvent volatilization upon application.

A Pickering emulsion method which involves adsorbing a powder onto the interface between an oil phase and a water phase for emulsification is known as a method for producing an oil-in-water emulsion cosmetic without the use of a surfactant. However, an inorganic powder such as a metal oxide or a mineral (e.g., silica) is generally used as the powder for use in the method. However, these powders need to be blended in a large amount due to their weak emulsifying ability. Therefore, the resulting cosmetics disadvantageously offer powderiness or squeaky feeling. Furthermore, oil droplets emulsified with an inorganic powder disadvantageously have low stability because these oil droplets are vulnerable to impact and are easily unified by stirring or shaking (Patent Literature 1).

It is also known that a core-corona microgel (which corresponds to the core-corona polymer particle according to the present invention) obtained by radical-polymerizing a specific polyethylene oxide macromonomer, a specific acrylate derivative monomer, and a specific cross-linkable monomer under specific conditions is very highly swellable in an organic solvent and can be stably emulsified in various types of oils. It has further been reported that an oil-in-water emulsion cosmetic having excellent emulsion stability, less sticky feeling, and less powderiness or squeaky feeling is obtained by using the microgel as an emulsifier. However, a water-in-oil emulsion cosmetic cannot be obtained even if the microgel is used as an emulsifier (Patent Literature 2).

Under these circumstances, there is a demand for the development of a core-corona microparticle excellent in emulsion stability, a raw material for a cosmetic, comprising the particle, and an oil-in-water emulsion cosmetic and a water-in-oil emulsion cosmetic stabilized with the particle.

CITATION LIST

Patent Literature

[Patent Literature 1] Japanese Unexamined Patent Application No. 2001-518111
[Patent Literature 2] Japanese Unexamined Patent Application No. 2006-161026

DISCLOSURE OF THE INVENTION

Problem to be Solved by the Invention

Accordingly, the present invention has been made in light of the conventional techniques. An object of the present invention is to provide a core-corona polymer particle that can be generally used not only in an oil-in-water emulsion cosmetic but in a water-in-oil emulsion cosmetic. Another object of the present invention is to provide an oil-in-water emulsion cosmetic and a water-in-oil emulsion cosmetic emulsified with the microparticle having excellent emulsion stability, less sticky feeling, and less powderiness or squeaky feeling.

Means to Solve the Problem

The present inventors have conducted diligent studies to attain the objects mentioned above and consequently found that a core-corona polymer particle that can be generally used in an oil-in-water emulsion cosmetic and a water-in-oil emulsion cosmetic is obtained by radical-polymerizing a specific polyethylene oxide macromonomer and a specific silicone derivative monomer and/or acrylate derivative monomer under specific conditions. The present inventors have further found that an oil-in-water emulsion cosmetic and a water-in-oil emulsion cosmetic emulsified with the microparticle has excellent emulsion stability, less sticky feeling, and less powderiness or squeaky feeling.

Specifically, the core-corona polymer particle according to the present invention is obtained by radical-polymerizing a polyethylene oxide macromonomer represented by the following formula (1) and one or two or more of hydrophobic monomers represented by the following formulas (2) and (3) under the following conditions (A) to (D):
(A-1) the macromonomer represented by the following formula (1) is an acrylic acid derivative or a methacrylic acid derivative containing a polyethylene glycol group having 8 to 200 repeat units;
(A-2) the acrylate derivative monomer represented by the following formula (2) is an acrylic acid derivative or a methacrylic acid derivative having a substituent containing an alkyl group having 1 to 12 carbon atoms;

(A-3) the silicone derivative monomer represented by the following formula (3) is an acrylic acid derivative or a methacrylic acid derivative having a substituent containing polydimethylsiloxane;

(B) a molar ratio represented by molar quantity of the polyethylene oxide macromonomer added/molar quantity of (the hydrophobic monomer) added is 1:10 to 1:250;

(C) a polymerization solvent is a water-alcohol mixed solvent, and the alcohol is one or two or more members selected from ethanol, dipropylene glycol, 1,3-butylene glycol, and isoprene glycol; and (D) solvent composition of the water-alcohol mixed solvent is water:alcohol=50 to 10:50 to 90 in terms of a mass ratio at 20° C.:

[Formula 1]

$$\underset{O}{\overset{R_1}{\underset{\|}{\diagup\!\!\!\diagdown}}}\!\!\!\!\!-\!O\!\!-\!\!(CH_2\!\!-\!\!CH_2\!\!-\!\!O)_n\!\!-\!X \quad (1)$$

wherein $R_1$ represents hydrogen or a hydrocarbon group having 1 to 3 carbon atoms, X represents hydrogen or a methyl group, and n represents a number of 8 to 200;

[Formula 2]

$$\underset{O}{\overset{R_2}{\underset{\|}{\diagup\!\!\!\diagdown}}}\!\!\!\!\!-\!O\!-\!R_3 \quad (2)$$

wherein $R_2$ represents hydrogen or a hydrocarbon group having 1 to 3 carbon atoms, and $R_3$ represents a hydrocarbon group having 1 to 12 carbon atoms;

[Formula 3]

$$CH_2\!\!=\!\!\underset{\underset{O}{\|}}{\overset{R_1}{C}}\!\!-\!C\!-\!O\!-\!\underset{Me}{\overset{Me}{Si}}O\!\!-\!\!\left[\underset{Me}{\overset{Me}{Si}}O\right]_m\!\!-\!\!\underset{Me}{\overset{Me}{Si}}\!-\!R_3 \quad (3)$$

wherein $R_1$ represents hydrogen or a hydrocarbon group having 1 to 3 carbon atoms,
R3 represents a methyl group, and m represents an integer of 10 to 40.

The core-corona polymer particle is preferably used as a raw material for a cosmetic.

The core-corona polymer particle is preferably used as an emulsifier.

The core-corona polymer particle is preferably used as a clouding agent.

A particle size of the core-corona polymer particle is preferably 50 to 600 nm.

The core-corona polymer particle preferably comprises a cross-linking agent.

Effect of the Invention

According to the present invention, it has been found that a core-corona polymer particle that can be generally used in an oil-in-water emulsion cosmetic and a water-in-oil emulsion cosmetic is obtained by radical-polymerizing a specific polyethylene oxide macromonomer and a specific silicone derivative monomer and/or acrylate derivative monomer under specific conditions. It has further been found that an oil-in-water emulsion cosmetic and a water-in-oil emulsion cosmetic emulsified with the microparticle has excellent emulsion stability, less sticky feeling, and less powderiness or squeaky feeling.

BEST MODE FOR CARRYING OUT THE INVENTION

The core-corona polymer particle according to the present invention is obtained by radical-polymerizing a polyethylene oxide macromonomer represented by the formula (1) given below and one or two or more of hydrophobic monomers represented by the formulas (2) and (3) given below under conditions (A) to (D) given below.

The polyethylene oxide macromonomer used in the present invention is represented by the following formula (1):

[Formula 1]

$$\underset{O}{\overset{R_1}{\underset{\|}{\diagup\!\!\!\diagdown}}}\!\!\!\!\!-\!O\!\!-\!\!(CH_2\!\!-\!\!CH_2\!\!-\!\!O)_n\!\!-\!X \quad (1)$$

In the chemical formula (1), $R_1$ represents hydrogen or a hydrocarbon group having 1 to 3 carbon atoms, X represents hydrogen or a methyl group, and n represents a number of 8 to 200.

<Condition A1>

Condition A1 is that the polyethylene oxide macromonomer represented by the chemical formula (1) is an acrylic acid derivative or a methacrylic acid derivative containing a polyethylene glycol group having 8 to 200 repeat units.

The molecular weight of the polyethylene oxide macromonomer represented by the chemical formula (1) is preferably 350 to 9000.

The polyethylene oxide macromonomer used in the present invention can be a commercially available product. Examples thereof include commercially available products manufactured by Sigma-Aldrich Co. LLC, and Blemmer® manufactured by NOF Corp.

The hydrophobic monomer used in the present invention can be preferably an acrylate derivative monomer represented by the formula (2) given below and/or a silicone derivative monomer of the formula (3) given below.

The acrylate derivative monomer used in the present invention is represented by the following formula (2):

[Formula 2]

(2)

In the formula (2), $R_2$ represents hydrogen or a hydrocarbon group having 1 to 3 carbon atoms. $R_3$ represents a hydrocarbon group having 1 to 12 carbon atoms.

<Condition A2>

Condition A2 is that the acrylate derivative monomer represented by the formula (2) is an acrylic acid derivative or a methacrylic acid derivative having a substituent containing an alkyl group having 1 to 12 carbon atoms.

The acrylate derivative monomer used in the present invention is a general-purpose raw material and can be easily obtained as a general industrial raw material. For example, a commercially available product from Sigma-Aldrich Co. LLC or Tokyo Chemical Industry Co., Ltd. can be used.

The silicone derivative monomer used in the present invention is represented by the following formula (3):

[Formula 3]

(3)

In the formula (3), R1 represents hydrogen or a hydrocarbon group having 1 to 3 carbon atoms, R3 represents a methyl group, and m represents an integer of 10 to 40.

<Condition A3>

Condition A3 is that the silicone derivative monomer of the formula (3) is an acrylic acid derivative or a methacrylic acid derivative having a substituent containing polydimethylsiloxane.

The silicone derivative monomer used in the present invention can be a commercially available product from Shin-Etsu Chemical Co., Ltd., AZmax. Co., etc.

<Condition B>

Condition B is that a molar ratio represented by molar quantity of the polyethylene oxide macromonomer added/molar quantity of (the hydrophobic monomer) added is 1:10 to 1:250. If the molar ratio is less than 1:10, no core-corona particle may be formed because the polymer becomes hydrophilic. If the molar ratio exceeds 1:250, particles may be aggregated and precipitated because the polymer becomes hydrophobic.

<Condition C>

Condition C is that a polymerization solvent is a water-alcohol mixed solvent, and the alcohol is one or two or more members selected from ethanol, dipropylene glycol, 1,3-butylene glycol, and isoprene glycol.

<Condition D>

Condition D is that solvent composition of the water-alcohol mixed solvent is water:alcohol=90 to 10:10 to 90 in terms of a mass ratio at 20° C. Water:alcohol=50 to 10:90 to 50 is more preferred.

For the core-corona polymer particle according to the present invention, ethylene glycol dimethacrylate represented by the following formula (4) or N,N-methylenebisacrylamide of the following formula (5) can be used as a cross-linking agent in polymerizing the polyethylene oxide macromonomer represented by the following formula (1) and one or two or more of the hydrophobic monomers represented by the following formulas (2) and (3).

[Formula 4]

(4)

[Formula 5]

(5)

The amount of the cross-linking agent blended is preferably 1% by mass or less with respect to the acrylic acid derivatives or the methacrylic acid derivatives excluding the polyethylene oxide macromonomer.

The core-corona polymer particle according to the present invention is preferably 0.01 to 10% by mass, more preferably 0.05 to 5% by mass, still more preferably 0.05 to 2% by mass, based on the pure content of the core-corona polymer particle with respect to the total amount of a cosmetic. If the amount of the core-corona polymer particle blended is less than 0.01% by mass, a stable cosmetic may not be obtained. If the amount of the core-corona polymer particle blended exceeds 10% by mass, stability may be poor in long-term preservation under high-temperature conditions or feeling of use may be poor.

The particle size of the core-corona polymer particle according to the present invention is preferably 50 to 600 nm. If the particle size is less than 50 nm, cloudiness may be markedly reduced. If the particle size exceeds 600 nm, particles may be precipitated or a function as an emulsifier may be deactivated.

Figure 1:
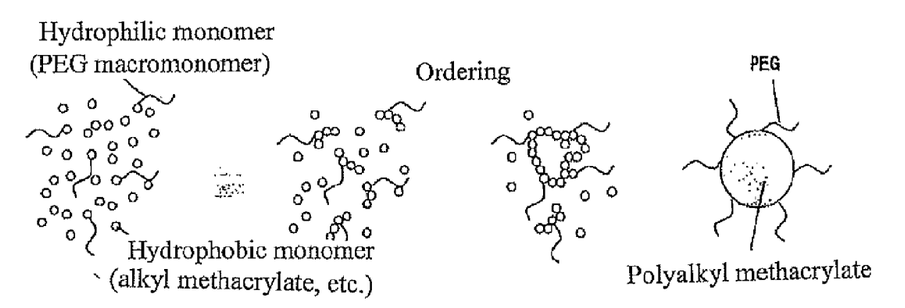
FIG. 1 is a schematic view showing a microgel formation mechanism of the core-corona polymer particle of the present invention.

As for the core-corona polymer particle according to the present invention, the present inventor has presumed that hydrophilic macromonomers and hydrophobic monomers are ordered, as shown in FIG. 1, in a solvent to form a core-corona polymer particle dispersion having an almost constant particle size and containing a cross-linked core moiety.

However, it has so far been impossible or substantially impractically difficult to completely identify the presence of this core-corona polymer particle in the state as shown in FIG. 1. Thus, it has been impossible to identify the invention of a product related to the present invention as the configuration of the product itself. Accordingly, this product-by-process invention is clear.

The core-corona polymer particle according to the present invention can be used in various cosmetic emulsifiers, clouding agents, raw materials for cosmetics, and the like.

In the case of blending the core-corona polymer particle according to the present invention into a cosmetic such as a cloudy cosmetic, the cosmetic is produced by mixing and dispersing the raw material for a cosmetic in a water phase or an oil phase according to a routine method.

The amount of the core-corona polymer particle of the present invention blended in the cosmetic is usually preferably 0.01 to 10% by mass (pure content; hereinafter, simply referred to as %) with respect to the total amount of the cosmetic. If the amount of the core-corona polymer particle blended is less than 0.01% (pure content), a stable cosmetic may be difficult to obtain. If the amount of the core-corona polymer particle blended exceeds 10% (pure content), the resulting cosmetic is not preferred from the viewpoint of stability in long-term preservation under high-temperature conditions or feeling of use may be poor.

The core-corona polymer particle according to the present invention may be blended as an excellent Pickering emulsion emulsifier into a cosmetic.

For functioning as an emulsifier, it is required that the molecular weight of the hydrophilic monomer should be 1500 to 9000. If the molecular weight is less than 1500, particles are strongly aggregated in a water phase and therefore cancel emulsifying ability. If the molecular weight exceeds 9000, too strong hydrophilicity cancels emulsifying ability.

(Oil-in-Water Emulsion Cosmetic)

The core-corona polymer particle of the present invention emulsifies an oil phase component and a water phase component to form an oil-in-water emulsion cosmetic having a structure where the core-corona microgel emulsifier is adsorbed on oil droplets of the oil phase component dispersed in the water phase component. Thus, the core-corona polymer particle of the present invention is excellent in emulsifying power. Furthermore, use of the raw material for a cosmetic of the present invention as an emulsifier can produce an oil-in-water emulsion cosmetic excellent in emulsion stability.

The oil-in-water emulsion cosmetic of the present invention is produced by mixing and dispersing the raw material for a cosmetic in water or a water phase component, and adding thereto an oil phase component and other components according to a routine method, followed by emulsification by stirring and application of shear force.

For preparing the core-corona polymer particle of the present invention into an oil-in-water cosmetic, the ratio of silicone-modified methacrylate to all the hydrophobic monomers is preferably 10% by mol or less. If the ratio is more than 10% by mol, a water-in-oil cosmetic may be formed.

(Water-in-Oil Emulsion Cosmetic)

The core-corona polymer particle of the present invention can also emulsify an oil phase component and a water phase component to form a water-in-oil emulsion cosmetic having a structure where the core-corona microgel emulsifier is adsorbed on water droplets of the water phase component dispersed in the oil phase component.

The water-in-oil emulsion cosmetic of the present invention is produced by mixing and dispersing the raw material for a cosmetic in an oil or an oil phase component, and adding thereto a water phase component and other components according to a routine method, followed by emulsification by stirring and application of shear force.

For preparing the core-corona polymer particle of the present invention into a water-in-oil cosmetic, the ratio of silicone-modified methacrylate to all the hydrophobic monomers is preferably more than 10% by mol.

[Other Components]

The cosmetic comprising the core-corona polymer particle according to the present invention can be produced according to a routine method depending on the dosage form of interest by appropriately blending, if necessary, other components, for example, an inorganic powder, an organic powder, an ester, an anionic surfactant, a cationic surfactant, an amphoteric surfactant, a nonionic surfactant, a moisturizing agent, a water-soluble polymer, a thickener, a film-forming agent, an ultraviolet absorber, a sequestering agent, a lower alcohol, a polyhydric alcohol, a sugar, an amino acid, an organic amine, a polymer emulsion, a pH adjuster, a skin nutrient, a vitamin, an antioxidant, an antioxidative aid, a fragrance, and water, without impairing the effect of the present invention.

Examples of the inorganic powder include talc, boron nitride, sericite, natural mica, calcined mica, synthetic mica, synthetic sericite, alumina, mica, kaolin, bentonite, smectite, calcium carbonate, magnesium carbonate, calcium phosphate, silicic anhydride, magnesium oxide, tin oxide, iron oxide, yttrium oxide, chromium oxide, zinc oxide, cerium oxide, aluminum oxide, magnesium oxide, chromium hydroxide, iron blue, ultramarine, calcium phosphate, aluminum hydroxide, barium sulfate, magnesium sulfate, silicic acid, aluminum magnesium silicate, calcium silicate, barium silicate, magnesium silicate, aluminum silicate, strontium silicate, silicon carbide, magnesium fluoride, tungstic acid metal salts, magnesium aluminate, magnesium aluminometasilicate, chlorohydroxyaluminum, clay, zeolite, hydroxyapatite, ceramic powders, spinel, mullite, cordierite, aluminum nitride, titanium nitride, silicon nitride, lanthanum, samarium, tantalum, terbium, europium, neodymium, Mn—Zn ferrite, Ni—Zn ferrite, silicon carbide, cobalt titanate, barium titanate, iron titanate, lithium cobalt titanate, cobalt aluminate, antimony-containing tin oxide, tin-containing indium oxide, magnetite, aluminum powders, gold powders, sliver powders, platinum powders, copper powders, noble metal colloids, iron powders, zinc powders, cobalt blue, cobalt violet, cobalt green, low-order titanium oxide, fine titanium oxide particles, butterfly-shaped barium sulfate, flower-shaped zinc oxide, tetrapod-shaped zinc oxide, fine zinc oxide particles, and pearl pigments such as titanium oxide-coated mica, titanium oxide-coated synthetic mica, titanium oxide-coated silica, titanium oxide-coated talc, zinc oxide-coated silica, titanium oxide-coated colored mica, red iron-coated titanated mica, red/black iron oxide-coated titanated mica, carmine-coated titanated mica, and iron blue-coated titanated mica.

Examples of the organic powder include (e.g., silicone elastomer powders, silicone powders, silicone resin-coated silicone elastomer powders, polyamide resin powders (nylon powders), polyethylene powders, polymethyl methacrylate powders (e.g., methyl methacrylate crosspolymers), polystyrene powders, styrene-acrylic acid copolymer resin powders, benzoguanamine resin powders, polytetrafluoroethylene powders, and cellulose powders); and organic pigments such as zirconium, barium and aluminum lake (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404.

Examples of the anionic surfactant include fatty acid soaps (e.g., sodium laurate and sodium palmitate); higher alkyl sulfuric acid ester salts (e.g., sodium lauryl sulfate and potassium lauryl sulfate); alkyl ether sulfuric acid ester salts (e.g., POE-triethanolamine lauryl sulfate and POE-sodium lauryl sulfate); N-acyl sarcosinates (e.g., lauroyl sarcosine sodium); higher fatty acid amide sulfonates (e.g., N-myristoyl-N-methyl taurine sodium, coconut oil fatty acid methyl taurid sodium, and methyl lauroyl taurate sodium); phosphoric acid ester salts (sodium POE-oleyl ether phosphate and POE-stearyl ether phosphoric acid); sulfosuccinates (e.g., sodium di-2-ethylhexylsulfosuccinate, sodium monolauroyl monoethanolamide polyoxyethylene sulfosuccinate, and sodium lauryl polypropylene glycol sulfosuccinate); alkylbenzenesulfonates (e.g., sodium linear dodecylbenzenesulfonate, triethanolamine linear dodecylbenzenesulfonate, and linear dodecylbenzenesulfonic acid); higher fatty acid ester sulfuric acid ester salts (e.g., sodium hydrogenated coconut oil fatty acid glycerin sulfate); N-acylglutamates (e.g., monosodium N-lauroyl glutamate, disodium N-stearoyl glutamate, and monosodium N-myristoyl-L-glutamate); sulfated oils (e.g., Turkey red oil); POE-alkyl ether carboxylic acids; POE-alkyl allyl ether carboxylates; α-olefin sulfonates; higher fatty acid ester sulfonates; secondary alcohol sulfuric acid ester salts; higher fatty acid alkylolamide sulfuric acid ester salts; sodium lauroyl monoethanolamide succinate; ditriethanolamine N-palmitoyl aspartate; and casein sodium.

Examples of the cationic surfactant include alkyl trimethyl ammonium salts (e.g., stearyl trimethyl ammonium chloride and lauryl trimethyl ammonium chloride); alkylpyridinium salts (e.g., cetylpyridinium chloride); distearyl dimethyl ammonium chloride dialkyl dimethyl ammonium salts; poly(N,N'-dimethyl-3,5-methylene piperidinium) chloride; alkyl quaternary ammonium salts; alkyl dimethyl benzyl ammonium salts; alkyl isoquinolinium salts; dialkyl morpholinium salts; POE-alkylamines; alkylamine salts; polyamine fatty acid derivatives; amyl alcohol fatty acid derivatives; benzalkonium chloride; and benzethonium chloride.

Examples of the amphoteric surfactant include imidazoline amphoteric surfactants (e.g., 2-undecyl-N,N,N-(hydroxyethylcarboxymethyl)-2-imidazoline sodium and 2-cocoyl-2-imidazolinium hydroxide-1-carboxyethyloxy di sodium salt); and betaine surfactants (e.g., 2-heptadecyl-N-carboxymethyl-N-hydroxyethyl imidazolinium betaine, betaine lauryl dimethylaminoacetate, alkyl betaine, amide betaine, and sulfobetaine).

Examples of the lipophilic nonionic surfactant include sorbitan fatty acid esters (e.g., sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerin polyglycerin fatty acids (e.g., mono-cottonseed oil fatty acid glycerin, glycerin monoerucate, glycerin sesquioleate, glycerin monostearate, pyroglutamic acid glycerin α,α-oleate, and malic acid glycerin monostearate); propylene glycol fatty acid esters (e.g., propylene glycol monostearate); hydrogenated castor oil derivatives; and glycerin alkyl ethers.

Examples of the hydrophilic nonionic surfactant include POE-sorbitan fatty acid esters (e.g., POE-sorbitan monooleate, POE-sorbitan monostearate, POE-sorbitan monooleate, and POE-sorbitan tetraoleate); POE-sorbitol fatty acid esters (e.g., POE-sorbitol monolaurate, POE-sorbitol monooleate, POE-sorbitol pentaoleate, and POE-sorbitol monostearate); POE-glycerin fatty acid esters (e.g., POE-monooleates such as POE-glycerin monostearate, POE-glycerin monoisostearate, and POE-glycerin triisostearate); POE-fatty acid esters (e.g., POE-distearate, POE-monodioleate, and ethylene glycol distearate); POE-alkyl ethers (e.g., POE-lauryl ether, POE-oleyl ether, POE-stearyl ether, POE-behenyl ether, POE-2-octyl dodecyl ether, and POE-cholestanol ether); Pluronic surfactants (e.g., Pluronic); POE.POP-alkyl ethers (e.g., POE.POP-cetyl ether, POE.POP-2-decyl tetradecyl ether, POE.POP-monobutyl ether, POE.POP-hydrogenated lanoline, and POE.POP-glycerin ether); tetra-POE/tetra-POP-ethylenediamine condensates (e.g., Tetronic); POE-castor oil hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid); POE-beeswax/lanoline derivatives (e.g., POE-sorbitol beeswax); alkanolamides (e.g., coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkyl ethoxy dimethylamine oxides; and trioleyl phosphoric acid.

Examples of the moisturizing agent include polyethylene glycol, propylene glycol, glycerin, 1,3-butylene glycol, xylitol, sorbitol, maltitol, chondroitin sulfate, hyaluronic acid, mucoitin sulfate, caronic acid, atelocollagen, cholesteryl-12-hydroxystearate, sodium lactate, bile acid salt, dl-pyrrolidone carboxylate, alkylene oxide derivatives, short-chain soluble collagen, diglycerin (EO) PO adducts, *Rosa roxburghii* fruit extracts, *Achillea millefolium* extracts, and melilot extracts.

Examples of the natural water-soluble polymer include plant-derived polymers (e.g., gum arabic, tragacanth gum, galactan, guar gum, carob gum, karaya gum, carrageenan, pectin, agar, quince seeds (marmelo), algae colloids (Fucus vesiculosus extracts), starch (rice, corn, potato, and wheat starches), and glycyrrhizic acid); microorganism-derived polymers (e.g., xanthan gum, dextran, succinoglucan, and pullulan); and animal-derived polymers (e.g., collagen, casein, albumin, and gelatin).

Examples of the semisynthetic water-soluble polymer include starch polymers (e.g., carboxymethyl starch and methylhydroxypropyl starch); cellulose polymers (methylcellulose, ethylcellulose, methylhydroxypropylcellulose, hydroxyethylcellulose, cellulose sodium sulfate, hydroxypropylcellulose, carboxymethylcellulose, carboxymethylcellulose sodium, crystalline cellulose, cellulose powders, etc.); and alginic acid polymers (e.g., sodium alginate and alginic acid propylene glycol ester).

Examples of the synthetic water-soluble polymer include vinyl polymers (e.g., polyvinyl alcohol, polyvinyl methyl ether, polyvinylpyrrolidone, and carboxyvinyl polymers); polyoxyethylene polymers (e.g., polyoxyethylene-polyoxypropylene copolymers of polyethylene glycol 20,000, 40,000, or 60,0000); acrylic polymers (e.g., sodium polyacrylate, polyethyl acrylate, and polyacrylamide); polyethylenimine; and cationic polymers.

Examples of the thickener include gum arabic, carrageenan, karaya gum, tragacanth gum, carob gum, quince seeds (marmelo), casein, dextrin, gelatin, sodium pectinate, sodium alginate, methylcellulose, ethylcellulose, CMC, hydroxyethylcellulose, hydroxypropylcellulose, PVA, PVM, PVP, sodium polyacrylate, carboxyvinyl polymers, locust bean gum, guar gum, tamarind gum, cellulose dialkyl dimethyl ammonium sulfate, xanthan gum, aluminum magnesium silicate, bentonite, hectorite, AlMg silicate (Veegum), laponite, and silicic anhydride.

Examples of the ultraviolet absorber include benzoic acid ultraviolet absorbers (e.g., p-aminobenzoic acid (hereinafter, abbreviated to PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid ultraviolet absorbers (e.g., homomenthyl-N-acetyl anthranilate); salicylic acid ultraviolet absorbers (e.g., amyl salicylate, menthyl salicylate, homomenthyl salicylate, octyl salicylate, phenyl salicylate, benzyl salicylate, and p-isopropanolphenyl salicylate); cinnamic acid ultraviolet absorbers (e.g., octylmethoxy cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-di-p-methoxy cinnamate); benzophenone ultraviolet absorbers (e.g., 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenylbenzotriazole; dibenzalazine; dianisoylmethane; 4-methoxy-4'-t-butyldibenzoylmethane; 5-(3,3-dimethyl-2-norbornylidene)-3-pentan-2-one and dimorpholinopyridazino; 2-ethylhexyl-2-cyano-3,3-diphenyl acrylate; and 2,4-bis-{[4-(2-ethylhexyloxy)-2-hydroxy]-phenyl}-6-(4-methoxyphenyl)-(1,3,5)-triazine.

Examples of the sequestering agent include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of the lower alcohol include ethanol, propanol, isopropanol, isobutyl alcohol, and t-butyl alcohol.

Examples of the polyhydric alcohol include dihydric alcohols (e.g., ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (e.g., glycerin and trimethylolpropane); tetrahydric alcohols (e.g., pentaerythritol such as 1,2,6-hexanetriol); pentahydric alcohols (e.g., xylitol); hexahydric alcohols (e.g., sorbitol and mannitol); polyhydric alcohol polymers (e.g., diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkyl ethers (e.g., ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin monoalkyl ethers (e.g., xyl alcohol, selachyl alcohol, and batyl alcohol); sugar alcohols (e.g., sorbitol, maltitol, maltotriose, mannitol, sucrose, erythritol, glucose, fructose, sugars obtained by starch decomposition, maltose, xylitose, and reduced alcohols of sugars obtained by starch decomposition); Glysolid; tetrahydrofurfuryl alcohol; POE-tetrahydrofurfuryl alcohol; POP-butyl ether; POP-.POE-butyl ether; tripolyoxypropylene glycerin ether; POP-glycerin ether; POP-glycerin ether phosphoric acid; and POP.POE-pentane erythritol ether and polyglycerin.

Examples of the monosaccharide include trioses (e.g., D-glyceryl aldehyde and dihydroxyacetone); tetroses (e.g., D-erythrose, D-erythrulose, D-threose, and erythritol); pentoses (e.g., L-arabinose, D-xylose, L-lyxose, D-arabinose, D-ribose, D-ribulose, D-xylulose, and L-xylulose); hexoses (e.g., D-glucose, D-talose, D-psicose, D-galactose, D-fructose, L-galactose, L-mannose, and D-tagatose); heptoses (e.g., aldoheptose and heplose); octoses (e.g., octulose); deoxy sugars (e.g., 2-deoxy-D-ribose, 6-deoxy-L-galactose, and 6-deoxy-L-mannose); amino sugars (e.g., D-glucosamine, D-galactosamine, sialic acid, aminouronic acid, and muramic acid); and uronic acids (e.g., D-glucuronic acid, D-mannuronic acid, L-gluronic acid, D-galacturonic acid, and L-iduronic acid).

Examples of the oligosaccharide include sucrose, gentianose, umbelliferose, lactose, planteose, isolychnoses, α,α-trehalose, raffinose, lychnoses, umbilicin, stachyose verbascoses.

Examples of the polysaccharide include cellulose, quince seeds, chondroitin sulfate, starch, galactan, dermatan sulfate, glycogen, gum arabic, heparan sulfate, hyaluronic acid, tragacanth gum, keratan sulfate, chondroitin, xanthan gum, mucoitin sulfate, guar gum, dextran, keratosulfate, locust bean gum, succinoglucan, and charonin.

Examples of the amino acid include neutral amino acids (e.g., threonine and cysteine); and basic amino acids (e.g., hydroxylysine). Examples of the amino acid derivative include acyl sarcosine sodium (lauroyl sarcosine sodium), acylglutamate, acyl β-alanine sodium, glutathione, and pyrrolidonecarboxylic acid.

Examples of the organic amine include monoethanolamine, diethanolamine, triethanolamine, morpholine, triisopropanolamine, 2-amino-2-methyl-1,3-propanediol, and 2-amino-2-methyl-1-propanol.

Examples of the polymer emulsion include acrylic resin emulsions, polyethyl acrylate emulsions, acrylic resin fluids, polyacrylic alkyl ester emulsions, polyvinyl acetate resin emulsions, and natural rubber latex.

Examples of the pH adjuster include buffers such as lactic acid-sodium lactate, citric acid-sodium citrate, and succinic acid-sodium succinate.

Examples of the vitamins include vitamins A, B1, B2, B6, C, E and derivatives thereof, pantothenic acid and derivatives thereof, and biotin.

Examples of the antioxidant include tocopherols, dibutylhydroxytoluene, butylhydroxyanisole, and gallic acid esters.

Examples of the antioxidative aid include phosphoric acid, citric acid, ascorbic acid, maleic acid, malonic acid, succinic acid, fumaric acid, kephalin, hexametaphosphate, phytic acid, and ethylenediaminetetraacetic acid.

Examples of other components that may be blended include antiseptics (ethylparaben, butylparaben, chlorphenesin, phenoxyethanol, etc.); antiphlogistics (e.g., glycyrrhizic acid derivatives, glycyrrhetinic acid derivatives, salicylic acid derivatives, hinokitiol, zinc oxide, and allantoin); skin-lightening agents (e.g., placenta extracts, *Saxifraga stolonifera* extracts, and arbutin); various extracts (e.g., phellodendron bark, coptis rhizome, lithospermum root, *Paeonia lactiflora*, swertia herb, birch, sage, loquat, carrot, aloe, mallow, iris, grape, coix seed, luffa, lily, saffron, cnidium rhizome, ginger, hypericum, Ononis, garlic, capsicum, citrus unshiu peel, Japanese angelica root, and algae), activators (e.g., royal jelly, photosensitizers, and cholesterol derivatives); blood flow stimulants (e.g., nonanoic acid vanillylamide, nicotinic acid benzyl ester, nicotinic acid β-butoxy ethyl ester, capsaicin, zingerone, cantharides tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol); anti-seborrheic agents (e.g., sulfur and thianthol); and anti-inflammatory agents (e.g., tranexamic acid, thiotaurine, and hypotaurine).

Further, for example, sequestering agents such as disodium edetate, trisodium edetate, sodium citrate, sodium polyphosphate, sodium metaphosphate, gluconic acid, and malic acid, various crude drug extracts such as caffein, tannin, verapamil, tranexamic acid and derivatives thereof, licorice, Chinese quince, and *Pyrola japonica*, chemicals such as tocopherol acetate, glycyrrhetinic acid, glycyrrhizic acid and derivatives thereof and salts thereof, skin lightening agents such as vitamin C, magnesium ascorbyl phosphate, glucoside ascorbate, arbutin, and kojic acid, amino acids such as arginine and lysine and derivatives thereof, and sugars such as fructose, mannose, erythritol, trehalose, and xylitol can be appropriately blended.

The product form of the raw material for a cosmetic, comprising the core-corona polymer particle according to the present invention can adopt every product form. Specifically, product forms such as lotions, milky lotions, beauty essences, creams, sunscreens, and liquid foundations can be adopted.

[Method for Producing Core-Corona Polymer Particle]

The core-corona polymer particle can be produced by a method known in the art. The method is, for example, as follows: to a three-neck flask equipped with a reflux tube and a nitrogen feed tube, a predetermined solvent (e.g., a water-alcohol mixed solvent) is added, and a polyethylene oxide monomer and hydrophobic monomers are added. After sufficient dissolution or dispersion, the flask is purged with nitrogen for 20 minutes or longer to remove dissolved oxygen. Then, 1% by mol of a radical polymerization initiator with respect to the total amount of the monomers is added and dissolved. The polymerization solution with homogeneous dissolution or dispersion is purged with nitrogen to remove dissolved oxygen. Then, polymerization reaction is performed for 8 hours at a temperature kept at 65 to 70° C. in an oil bath with stirring. After the completion of polymerization, a core-corona polymer particle dispersion is obtained.

[Method for Producing Cosmetic Comprising Core-Corona Polymer Particle According to Present Invention]

The cosmetic can be produced by a method known in the art. Examples thereof include a method of adding a predetermined solubilizer and oil into water containing the core-corona polymer particle to obtain a solubilized lotion, and a method of adding an oil into water containing the core-corona polymer particle and a water-soluble thickener, and then applying strong shear force thereto using a homomixer to obtain a milky lotion.

EXAMPLES

Hereinafter, the present invention will be described in more detail with reference to Examples. However, the present invention is not limited thereby. The amounts of components blended are indicated by % by mass with respect to the system into which the components are to be blended, unless otherwise specified.

[Core-Corona Polymer Particle]

First, methods for evaluating the core-corona polymer particle according to the present invention will be described.

Evaluation (1): Evaluation of Appearance

The appearance of core-corona polymer particles was observed and evaluated according to the following criteria.

(Evaluation Criteria)

A: The core-corona polymer particles were homogeneous without separation and/or aggregates.

B: The core-corona polymer particles were almost homogeneous, though separation and/or aggregates were slightly observed.

C: The core-corona polymer particles were not homogeneous, and separation and/or aggregates were markedly observed.

Evaluation (2): Evaluation of Particle Size and Degree of Dispersion

The particle size of a core-corona microgel was measured using Zetasizer manufactured by Malvern Panalytical Ltd. A measurement sample having a microgel concentration of approximately 0.1% was prepared by the water dilution of a microgel dispersion and passed through a 0.45 micrometer filter to remove trash. Then, scattering intensity at 25° C. was measured at a scattering angle of 173° (backscattered light). An average particle size and a degree of dispersion were calculated using analysis software installed in the measurement apparatus.

The particle size was analyzed by the cumulant analysis method, and the degree of dispersion was a numerical value obtained by normalizing a secondary cumulant value obtained by cumulant analysis. This degree of dispersion is a parameter generally used and can be automatically analyzed using a commercially available dynamic light scattering measurement apparatus. The viscosity of pure water, i.e., 0.89 mPa·s at 25° C., was used as the viscosity of the solvent necessary for particle size analysis.

First, the present inventors evaluated the core-corona polymer particle according to the present invention by the evaluation methods. The amount of each component blended is described in Table 1. Conditions for radical-polymerizing components are described in Table 2. Each evaluation of the obtained raw material for a cosmetic is described in Table 3.

A hydrophilic monomer represented by the formula (1) and a hydrophobic monomer represented by the following formula (3) (silicone-modified methacrylate) were used in production.

TABLE 1

|  | Hydrophilic monomer | | Hydrophobic monomer | | | Polymerization solvent | |
|---|---|---|---|---|---|---|---|
|  | Methoxy PEG | | Silicone-modified methacrylate | | | | |
|  | Mw = 1000 | Mw = 4000 | Mw = 900 | Mw = 2300 | Mw = 12000 | | |
|  | Formula (1) | Formula (1) | Formula (3) | Formula (3) | Formula (3) | Water | Ethanol |
| Comparative Production Example 1 |  | 0.84 | 9.16 |  |  | 72 | 18 |
| Comparative Production Example 2 |  | 0.84 | 9.16 |  |  | 45 | 45 |
| Production Example 3 |  | 0.84 | 9.16 |  |  | 18 | 72 |
| Production Example 4 |  | 0.84 | 9.16 |  |  | 9 | 81 |
| Production Example 5 | 0.25 |  | 9.75 |  |  | 18 | 72 |
| Production Example 6 |  | 0.67 |  | 9.33 |  | 18 | 72 |
| Comparative Production Example 7 |  | 0.65 |  |  | 9.35 | 18 | 72 |
| Production Example 8 |  | 1.66 | 8.44 |  |  | 18 | 72 |

TABLE 2

|  | (A-1)Hydrophilic macromonomer Formula(1) | (A-3)Hydrophobic macromonomer Formula(3) | (B)Hydrophilic macromonomer/ Hydrophobic macromonomer ratio (molar ratio) |
|---|---|---|---|
| Comparative Production Example1 | R1 = CH3, n = 90 | $R_1$ = CH$_3$, m = 12, $R_3$ = CH$_3$ | 1/50 |
| Comparative Production Example2 | R1 = CH3, n = 90 | $R_1$ = CH$_3$, m = 12, $R_3$ = CH$_3$ | 1/50 |
| Production Example3 | R1 = CH3, n = 90 | $R_1$ = CH$_3$, m = 12, $R_3$ = CH$_3$ | 1/50 |
| Production Example4 | R1 = CH3, n = 90 | $R_1$ = CH$_3$, m = 12, $R_3$ = CH$_3$ | 1/50 |
| Production Example5 | R1 = CH3, n = 20 | $R_1$ = CH$_3$, m = 12, $R_3$ = CH$_3$ | 1/50 |
| Production Example6 | R1 = CH3, n = 90 | $R_1$ = CH$_3$, m = 23, $R_3$ = CH$_3$ | 1/25 |
| Comparative Production Example7 | R1 = CH3, n = 90 | $R_1$ = CH$_3$, m = 46, $R_3$ = CH$_3$ | 1/5 |
| Production Example8 | R1 = CH3, n = 90 | $R_1$ = CH$_3$, m = 12, $R_3$ = CH$_3$ | 1/25 |

TABLE 3

|  | Evaluation(1) Appearance | Evaluation(2) Particle size (nm) | Evaluation (2) Degree of dispersion |
|---|---|---|---|
| Comparative Production Example1 | C | Immeasurable | Immeasurable |
| Comparative Production Example2 | C | Immeasurable | Immeasurable |
| Production Example3 | B | 530 | 0.13 |
| Production Example4 | A | 400 | 0.10 |
| Production Example5 | B | 430 | 0.12 |
| Production Example6 | B | 550 | 0.23 |
| Comparative Production Example7 | C | Immeasurable | Immeasurable |
| Production Example8 | A | 340 | 0.21 |

From Production Examples 3 and 6 and Comparative Production Example 7, it is evident that if silicone chain length m in the hydrophobic monomer is 46 or more, dispersion is nonuniform and core-corona polymer particles are not accurately formed or strongly aggregated.

Comparative Production Examples 1 and 2 revealed that if the water-alcohol mixed solvent has composition richer in water than 45:45, dispersion is nonuniform and core-corona polymer particles are not accurately formed or strongly aggregated.

Next, a cosmetic raw material was produced using a hydrophilic monomer represented by the formula (1) and two hydrophobic monomers represented by the following formulas (2) and (3), respectively. The amount of each component blended is described in Table 4. Conditions for radical-polymerizing components are described in Table 5. Each evaluation of the obtained raw material for a cosmetic is described in Table 6.

TABLE 4

|  | Hydrophilic macromonomer Methoxy PEG Mw = 4000 Formula(1) | Hydrophobic monomer | | Polimerization solvent | |
|---|---|---|---|---|---|
|  |  | Methyl methacrylate Formula (2) | Silicone-modified methacrylate Mw = 900 Formula(3) | Water | Ethanol |
| Production Example9 | 3.16 | 4.25 | 2.99 | 18 | 72 |
| Production Example10 | 1.37 | 1.77 | 7.44 | 18 | 72 |
| Production Example11 | 0.92 | 0.16 | 8.92 | 18 | 72 |

TABLE 5

|  | (A-1) Hydrophilic macromonomer Formula(1) | (A-2) Acrylate derivativemonomer Formula(2) | (A-3) Hydrophobic macromonomer Formula(3) | (B)Hydrophilic macromonomer/ total hydrophobic monomer ratio (molar ratio) | Acrylate derivativemonomer/ total hydrophobic monomer (mol %) |
|---|---|---|---|---|---|
| Production Example9 | R1 = CH3, n = 90 | $R_2$ = $CH_3$, $R_3$ = $CH_3$ | $R_1$ = $CH_3$, m = 12, $R_3$ = $CH_3$ | 1/50 | 90 |
| Production Example10 | R1 = CH3, n = 90 | $R_2$ = $CH_3$, $R_3$ = $CH_3$ | $R_1$ = $CH_3$, m = 12, $R_3$ = $CH_3$ | 1/50 | 50 |
| Production Example11 | R1 = CH3, n = 90 | $R_2$ = $CH_3$, $R_3$ = $CH_3$ | $R_1$ = $CH_3$, m = 12, $R_3$ = $CH_3$ | 1/50 | 10 |

TABLE 6

|  | Evaluation(1) Appearance | Evaluation(2) Particle size (nm) | Evaluation(2) Degree of dispersion |
|---|---|---|---|
| Production Example9 | A | 190 | 0.33 |
| Production Example10 | A | 230 | 0.23 |
| Production Example11 | A | 340 | 0.14 |

The core-corona polymer particles obtained in Production Examples 9 to 11 were dispersed. Specifically, core-corona polymer particles were found to be formed even when 10 to 90% by mol of the acrylate derivative monomer is included in all the hydrophobic monomers.

Next, the cosmetic raw material of the present invention was produced by further adding a cross-linking agent. The amount of each component blended is described in Table 7. Conditions for radical-polymerizing components are described in Table 8. Each evaluation of the obtained raw material for a cosmetic is described in Table 9.

TABLE 7

|  | Hydrophilic macromonomer | | Hydrophobic monomer Silicone-modified | Cross-linking agent | | |
|---|---|---|---|---|---|---|
|  | Methoxy PEG | | methacrylate | Ethylene glycol | Polymerization | |
|  | Mw = 1000 | Mw = 4000 | Mw = 900 | dimethacrylate | solvent | |
|  | Formula (1) | Formula (1) | Formula (3) | Formula (4) | Water | Ethanol |
| Pruduction Example 12 | 0.84 | | 9.11 | 0.05 | 18 | 72 |
| Comparative Production Example 13 | 0.71 | | 7.74 | 1.55 | 18 | 72 |

TABLE 8

|  | (A-1)Hydrophilic macromonomer Formula(1) | (A-3)Hydrophobic macromonomer Formula(3) | (B)Hydrophilic macromonomer/ Hydrophobic macromonomer ratio (molar ratio) | Cross-linking agent concentration (monomer ratio wt %) |
|---|---|---|---|---|
| Production Example12 | R1 = CH3, n = 90 | $R_1$ = CH$_3$, m = 12, $R_3$ = CH$_3$ | 1/50 | 0.5 |
| Comparative Production Example 13 | R1 = CH3 | $R_1$ = CH$_3$, m = 12, $R_3$ = CH$_3$ | 1/50 | 10 |

TABLE 9

|  | Appearance | Particle size (nm) | Degree of dispersion |
|---|---|---|---|
| Production Example12 | A | 396.0 | 0.10 |
| Comparative Production Example 13 | C | Immeasurable | Immeasurable |

As seen from these Production Examples, the amount of the cross-linking agent blended is preferably 0.5% by mass or less. It was revealed that if the amount of the cross-linking agent blended exceeds 10% by mass, dispersion is nonuniform and core-corona polymer particles are not accurately formed or strongly aggregated.

Next, the present inventors used evaluations described below to study whether a raw material for a cosmetic, containing dispersed core-corona polymer particles obtained in each Production Example would function as an emulsifier.

Methods for evaluating a cosmetic comprising a cosmetic comprising the core-corona polymer particle of the present invention as an emulsifier, a raw material for a cosmetic rill be described.

Evaluation (1): Evaluation of Stability (Appearance)

The appearance of a sample was visually observed 1 day after its preparation and evaluated according to the following criteria.

(Evaluation Criteria)

A: The sample was homogeneous without oil floating and/or powder aggregation.

B: The sample was almost homogeneous, though oil floating and/or powder aggregation was slightly observed.

C: The sample was not homogeneous, or marked separation of the oil phase or powder aggregation was observed.

Evaluation (2): Evaluation of Emulsion Stability (Emulsified Particle)

Emulsified particles of a sample were observed under an optical microscope.

(Evaluation Criteria)

A: The emulsified particles were homogeneous and were neither unified nor aggregated.

B: The emulsified particles were almost homogeneous, though slight unification, aggregation, or the like was observed.

C: The emulsified particles were not homogeneous, and marked unification and/or aggregation were observed.

Evaluation (3): Evaluation of Skin Irritation Test

An occluded patch was applied for 24 hours to the inner side of the upper arms of 10 panelists having sensitive skin. The state of the skin was determined according to the following criteria.

(Evaluation Criteria)

0 . . . No abnormality was observed.
1 . . . Slight redness was observed.
2 . . . Redness was observed.
3 . . . Redness and papula were observed.

Evaluation (4): Evaluation of Feeling of Use

Ten specialized panelists evaluated feeling of use ("refreshing feeling", "absence of stickiness", and "absence of squeaky feeling") upon application of a sample to the skin according to the following criteria.

(Evaluation Criteria)

A: 7 or more out of the 10 panelists answered "good" or "actually felt".
B: 5 or more out of the 10 panelists answered "good" or "actually felt".
C: 3 or more out of the 10 panelists answered "good" or "actually felt".
D: 2 or less out of the 10 panelists answered "good" or "actually felt".

Evaluation (5): Determination of Type of Emulsion

The type of an emulsion was determined as oil-in-water (O/W) when the electroconductivity of a sample was confirmed using a continuity test, and determined as water-in-oil (W/O) when no such electroconductivity was confirmed.

First, study was made on whether a raw material for a cosmetic, containing dispersed core-corona polymer particles obtained in Production Example 9 would function as an emulsifier.

TABLE 10

| Test Sample | 1-1 | 1-4 | 1-2 | 1-3 |
| --- | --- | --- | --- | --- |
| Ion-exchanged water | Balance | Balance | Balance | Balance |
| Dodecane | 50 | | | |
| Dimethicone | | 30 | 50 | 70 |
| Polymer particle described in Production Example 1 (based on pure content) | 1 | 1 | 1 | 1 |
| Ethanol | 10 | 10 | 10 | 10 |
| Carboxyvinyl polymer | 0.15 | 0.15 | 0.15 | 0.15 |
| Potassium hydroxide | 0.08 | 0.08 | 0.08 | 0.08 |
| Evaluation(1): emulsion stability(appearance) | A | A | A | A |
| Evaluation(2): emulsion stability(particle) | A | A | A | B |
| Evaluation(3): skin irritancy | O | O | O | O |
| Evaluation(4): refreshing feeling | A | A | A | B |
| Evaluation(4): absence of stickiness | A | A | A | A |
| Evaluation(4): absence of squeaky feeling | A | A | A | A |
| Evaluation(5): type of emulsion | O/W | O/W | O/W | O/W |

The obtained emulsion cosmetic was an oil-in-water emulsion cosmetic excellent in terms of stability, skin irritancy, and feeling of use.

Next, study was made on whether a raw material for a cosmetic, containing dispersed core-corona polymer particles obtained in Production Example 10, 11 and 3 would function as an emulsifier.

TABLE 11

| Test Sample | 1-5 | 1-8 | 1-6 | 1-7 |
| --- | --- | --- | --- | --- |
| Ion-exchanged water | Balance | Balance | Balance | Balance |
| Dodecane | 50 | | | |
| Dimethicone | | 30 | 50 | 70 |
| Polymer particle described in Production Example 10 (based on pure content) | 1 | 1 | 1 | 1 |
| Ethanol | 10 | 10 | 10 | 10 |
| Carboxyvinyl polymer | 0.15 | 0.15 | 0.15 | 0.15 |
| Potassium hydroxide | 0.08 | 0.08 | 0.08 | 0.08 |
| Evaluation(1): emulsion stability(appearance) | A | A | A | A |
| Evaluation(2): emulsion stability(particle) | A | B | A | A |
| Evaluation(3): skin irritancy | O | O | O | O |
| Evaluation(4): refreshing feeling | A | A | A | B |
| Evaluation(4): absence of stickiness | A | A | A | A |
| Evaluation(4): absence of squeaky feeling | A | A | A | A |
| Evaluation(5): type of emulsion | W/O | W/O | W/O | W/O |

TABLE 12

| Test Sample | 1-9 | 1-12 | 1-10 | 1-11 |
| --- | --- | --- | --- | --- |
| Ion-exchanged water | Balance | Balance | Balance | Balance |
| Dodecane | 50 | | | |
| Dimethicone | | 30 | 50 | 70 |
| Polymer particle described in Production Example 11 (based on pure content) | 1 | 1 | 1 | 1 |
| Ethanol | 10 | 10 | 10 | 10 |
| Carboxyvinyl polymer | 0.15 | 0.15 | 0.15 | 0.15 |
| Potassium hydroxide | 0.08 | 0.08 | 0.08 | 0.08 |
| Evaluation(1): emulsion stability(appearance) | A | A | A | A |
| Evaluation(2): emulsion stability(particle) | A | B | A | A |
| Evaluation(3): skin irritancy | O | O | O | O |
| Evaluation(4): refreshing feeling | A | A | A | B |
| Evaluation(4): absence of stickiness | A | A | A | A |
| Evaluation(4): absence of squeaky feeling | A | A | A | A |
| Evaluation(5): type of emulsion | W/O | W/O | W/O | W/O |

TABLE 13

| Test Sample | 1-13 | 1-16 | 1-14 | 1-15 |
| --- | --- | --- | --- | --- |
| Ion-exchanged water | Balance | Balance | Balance | Balance |
| Dodecane | 50 | | | |
| Dimethicone | | 30 | 50 | 70 |
| Polymer particle described in Production Example 3 (based on pure content) | 1 | 1 | 1 | 1 |
| Ethanol | 10 | 10 | 10 | 10 |
| Carboxyvinyl polymer | 0.15 | 0.15 | 0.15 | 0.15 |
| Potassium hydroxide | 0.08 | 0.08 | 0.08 | 0.08 |
| Evaluation(1): emulsion stability(appearance) | A | A | A | A |
| Evaluation(2): emulsion stability(particle) | A | B | A | A |
| Evaluation(3): skin irritancy | O | O | O | O |
| Evaluation(4): refreshing feeling | A | A | A | B |
| Evaluation(4): absence of stickiness | A | A | A | A |

TABLE 13-continued

| Test Sample | 1-13 | 1-16 | 1-14 | 1-15 |
|---|---|---|---|---|
| Evaluation(4): absence of squeaky feeling | A | A | A | A |
| Evaluation(5): type of emulsion | W/O | W/O | W/O | W/O |

When the acrylate derivative was 50% by weight or less with respect to the total amount of the hydrophobic monomers, the obtained emulsion cosmetic was found to be a water-in-oil emulsion cosmetic excellent in terms of stability, skin irritancy, and feeling of use.

Next, study was made on whether a raw material for a cosmetic, containing dispersed core-corona polymer particles obtained in Production Example 5 would function as an emulsifier.

TABLE 14

| Comparative Test Sample | 1-1 | 1-4 | 1-2 | 1-3 |
|---|---|---|---|---|
| Ion-exchanged water | Balance | Balance | Balance | Balance |
| Dodecane | 50 | | | |
| Dimethicone | | 30 | 50 | 70 |
| Polymer particle described in Production Example 5 (based on pure content) | 1 | 1 | 1 | 1 |
| Ethanol | 10 | 10 | 10 | 10 |
| Carboxyvinyl polymer | 0.15 | 0.15 | 0.15 | 0.15 |
| Potassium hydroxide | 0.08 | 0.08 | 0.08 | 0.08 |
| Evaluation(1): emulsion stability (appearance) | C | C | C | C |
| Evaluation(2): emulsion stability (particle) | C | C | C | C |
| Evaluation(3): skin irritancy | 0 | 0 | 0 | 0 |
| Evaluation(4): refreshing feeling | A | A | B | C |
| Evaluation(4): absence of stickiness | A | A | A | A |
| Evaluation (4): absence of squeaky feeling | A | A | A | A |
| Evaluation(5): type of emulsion | Undeterminable | Undeterminable | Undeterminable | Undeterminable |

| | 1-5 | 1-8 | 1-6 | 1-7 |
|---|---|---|---|---|
| | Balance | Balance | Balance | Balance |
| | 50 | | | |
| | | 30 | 50 | 70 |
| | 2 | 2 | 2 | 2 |
| | 10 | 10 | 10 | 10 |
| | 0.15 | 0.15 | 0.15 | 0.15 |
| | 0.08 | 0.08 | 0.08 | 0.08 |
| | C | C | C | C |
| | C | C | C | C |
| | 0 | 0 | 0 | 0 |
| | A | A | B | C |
| | A | A | A | A |
| | A | A | A | A |
| | Undeterminable | Undeterminable | Undeterminable | Undeterminable |

The raw material for a cosmetic, containing dispersed core-corona polymer particles obtained in Production Example 5 did not function as an emulsifier when a hydrophilic macropolymer having a molecular weight of 1000 or smaller was used.

Next, study was made on whether a raw material for a cosmetic, containing dispersed core-corona polymer particles obtained in Production Example 6 would function as an emulsifier.

TABLE 15

| | 1-17 | 1-19 |
|---|---|---|
| Ion-exchanged water | Balance | Balance |
| Dodecane | 50 | |
| Dimethicone | | 50 |
| Polymer particle described in Production Example 6 (based on pure content) | 1 | 1 |
| Ethanol | 10 | 10 |
| Carboxyvinyl polymer | 0.15 | 0.15 |
| Potassium hydroxide | 0.08 | 0.08 |
| Evaluation(1): emulsion stability(appearance) | A | A |
| Evaluation(2): emulsion stability(particle) | A | A |
| Evaluation(3): skin irritancy | 0 | 0 |
| Evaluation(4): refreshing feeling | A | A |

TABLE 15-continued

| | 1-17 | 1-19 |
|---|---|---|
| Evaluation(4): absence of stickiness | A | A |
| Evaluation(4): absence of squeaky feeling | A | A |
| Evaluation(5): type of emulsion | W/O | W/O |

The obtained emulsion cosmetic was an oil-in-water emulsion cosmetic or a water-in-oil emulsion cosmetic excellent in terms of stability, skin irritancy, and feeling of use.

Next, study was made on whether a raw material for a cosmetic, containing dispersed core-corona polymer particles obtained in Production Example 12 using a cross-linking agent would function as an emulsifier.

TABLE 16

|  | 1-21 | 1-22 | 1-23 | 1-24 |
|---|---|---|---|---|
| Ion-exchanged water | Balance | Balance | Balance | Balance |
| Dodecane | 50 | | | |
| Dimethicone | | 30 | 50 | 70 |
| Polymer particle described in Production Example 12 (based on pure content) | 1 | 1 | 1 | 1 |
| Ethanol | 10 | 10 | 10 | 10 |
| Carboxyvinyl polymer | 0.15 | 0.15 | 0.15 | 0.15 |
| Potassium hydroxide | 0.08 | 0.08 | 0.08 | 0.08 |
| Evaluation(1): emulsion stability(appearance) | A | A | A | A |
| Evaluation(2): emulsion stability(particle) | A | A | A | A |
| Evaluation(3): skin irritancy | 0 | 0 | 0 | 0 |
| Evaluation(4): refreshing feeling | A | A | A | B |
| Evaluation(4): absence of stickiness | A | A | A | A |
| Evaluation(4): absence of squeaky feeling | A | A | A | A |
| Evaluation(5): type of emulsion | W/O | W/O | W/O | W/O |

Use of the cosmetic raw material obtained using the cross-linking agent also produced a water-in-oil emulsion cosmetic excellent in terms of stability, skin irritancy, and feeling of use.

Next, study was made on whether a raw material for a cosmetic, containing dispersed core-corona polymer particles obtained in Production Example 8 would function as an emulsifier.

TABLE 17

|  | 1-25 | 1-26 | 1-27 | 1-28 |
|---|---|---|---|---|
| Ion-exchanged water | Balance | Balance | Balance | Balance |
| Dodecane | 50 | | | |
| Dimethicone | | 30 | 50 | 70 |
| Polymer particle described in Production Example 8 (based on pure content) | 1 | 1 | 1 | 1 |
| Ethanol | 10 | 10 | 10 | 10 |
| Carboxyvinyl polymer | 0.15 | 0.15 | 0.15 | 0.15 |
| Potassium hydroxide | 0.08 | 0.08 | 0.08 | 0.08 |
| Evaluation(1): emulsion stability(appearance) | A | A | A | A |
| Evaluation(2): emulsion stability(particle) | A | A | A | A |
| Evaluation(3): skin irritancy | 0 | 0 | 0 | 0 |
| Evaluation(4): refreshing feeling | A | A | A | B |
| Evaluation(4): absence of stickiness | A | A | A | A |
| Evaluation(4): absence of squeaky feeling | A | A | A | A |
| Evaluation(5): type of emulsion | W/O | W/O | W/O | W/O |

The obtained emulsion cosmetic was a water-in-oil emulsion cosmetic excellent in terms of stability, skin irritancy, and feeling of use. When the silicone chain length is short (m=12), the water-in-oil emulsion was found to be obtainable even if the hydrophilic monomer/hydrophobic monomer ratio was decreased (1/25).

What is claimed is:

1. A core-corona polymer particle obtained by radical-polymerizing a polyethylene oxide macromonomer and at least one hydrophobic monomer selected from the group consisting of an acrylate derivative monomer and a silicone derivative monomer, wherein the polyethylene oxide macromonomer is represented by the following formula (1):

wherein $R_1$ represents hydrogen or a hydrocarbon group having 1 to 3 carbon atoms, X represents hydrogen or a methyl group, and n represents a number from 8 to 200;

the acrylate derivative monomer is represented by the following formula (2):

wherein $R_2$ represents hydrogen or a hydrocarbon group having 1 to 3 carbon atoms, and $R_3$ represents a hydrocarbon group having 1 to 12 carbon atoms;

the silicone derivative monomer is represented by the following formula (3):

wherein $R_1$ represents hydrogen or a hydrocarbon group having 1 to 3 carbon atoms, $R_3$ represents a methyl group, and m represents an integer of 10 to 40;

a molar ratio represented by (molar quantity of the polyethylene oxide macromonomer added)/(molar quantity of the at least one hydrophobic monomer added) is 1:10 to 1:250;

a polymerization solvent is a water-alcohol mixed solvent, and the alcohol is one or two or more members selected from ethanol, dipropylene glycol, 1,3-butylene glycol, and isoprene glycol; and a mass ratio of water to the alcohol in the water-alcohol mixed solvent is 50:50 to 10:90 at 20° C.

2. An emulsifier comprising a core-corona polymer particle according to claim 1.

3. A clouding agent comprising a core-corona polymer particle according to claim 1.

4. The core-corona polymer particle according to claim 1, wherein a particle size of the core-corona polymer particle is 50 to 600 nm.

5. A cosmetic raw material comprising a core-corona polymer particle according to claim 1.

6. A raw material for a cosmetic, comprising a core-corona polymer particle according to claim 1 and ethylene glycol dimethacrylate as a cross-linking agent.

7. An oil-in-water emulsion cosmetic comprising a core-corona polymer particle according to claim 1.

8. A water-in-oil emulsion cosmetic comprising a core-corona polymer particle according to claim 1.

\* \* \* \* \*